US00PP08528P

United States Patent [19]

de Ruiter

[11] Patent Number: Plant 8,528

[45] Date of Patent: Jan. 4, 1994

[54] HYBRID TEA ROSE PLANT NAMED RUIROVINGT

[75] Inventor: Gijsbert de Ruiter, Hazerswoude, Netherlands

[73] Assignee: De Ruiter's Nieuwe Rozen B.V., Hazerswoude, Netherlands

[21] Appl. No.: 801,712

[22] Filed: Dec. 2, 1991

[51] Int. Cl.[5] ..... A01H 5/00

[52] U.S. Cl. ..... Plt./18

[58] Field of Search ..... Plt. 17, 18

*Primary Examiner*—Howard J. Locker

*Attorney, Agent, or Firm*—Christie, Parker & Hale

[57] ABSTRACT

A new variety of hybrid tea rose plant having apricot pink flowers suitable for growing under glass.

2 Drawing Sheets

SUMMARY OF THE INVENTION

The present invention relates to a new and distinct variety of rose plant of the hybrid tea rose class, which was originated by me by crossing as the seed parent the variety known as 'Korflapei', U.S. Plant Pat. No. 6,695, and as pollen parent the variety known as 'Kortexung', U.S. Plant No. 6,513. The varietal denomination of the new variety is 'Ruirovingt'.

Among the novel characteristics possessed by this new variety which distinguishes it from its parent and all other varieties of which I am aware are its flowers of multiple apricot and pink tones borne on a plant particularly suited for production of cut flowers under glass. The new variety can be reproduced through propagation by cuttings, grafting, budding and micropropagation, i.e. tissue culture. Flowers of the new variety are long lasting on the plant and after cutting. Asexual reproduction by budding, grafting, propagation of cuttings or micropropagation of the new variety as performed in Hazerswoude, Holland, shows that the foregoing and other distinguuishing characteristics come true to form and are established and transmitted through succeeding propagations.

BRIEF DESCRIPTION OF ILLUSTRATIONS

The accompanying illustrations show typical specimens of the vegetative growth and flowers of the new variety in different stages of development depicted in color as nearly true as it is reasonably possible to make the same in a color illustration of this character. Colors may vary depending upon growing conditions under different climate, soil, and cultivation conditions.

One illustration shows cut flowers of the new variety and is included to show flower form but the colors depicted are not true, due to the photo reproduction techniques employed for this illustration. The other illustration shows details of the illustration in color believed to more accurately depict flower coloration.

DETAILED DESCRIPTION OF THE NEW VARIETY

The following is a detailed description of my new variety, with color terminology in accordance with the Royal Horticultural Society Colour Chart (R.H.S.C.C.) and horticultural terminology in accordance with standard terminology used in UPOV-approved horticultural guidelines. The terminology used in color descriptions herein refers to plate numbers in the aforementioned color chart.

Parentage: Seedling.

*Seed parent.*—'Korflapei'.

*Pollen parent.*—'Kortexung'.

Class: Hybrid tea.

As can be seen in the accompanying illustrations, the detail illustration depicts the top of a young shoot, 1; compound three and five leaflet leaves, 2 and 3, respectively; stem, 4 and 5; buds, 6 and 7; a flower, 8, about one-half open; and a flower 9, more fully open. Also shown are flower stems 10, 11 and 12, with reproductive organs. The other illustration shows the new variety's attractive form as a cut flower.

The following further horticultural observations were made of specimens grown under glass in Holland.

Flower

Blooming habit: Nearly continuous.

A. Bud:

(1) *Size.*—Medium.

(2) *Form.*—Pointed, ovoid (before separation of sepals); urn shaped after sepals part.

(3) *Color.*—As sepals divide, bud color is near 36A.

(4) *Sepals.*—Slightly longer than bud, simple to slightly foliated.

(5) *Peduncle.*—Length — medium. Aspect — straight. Strength — erect. Color — medium green, near 139C.

B. Bloom:

*Flower.*—Medium size for cut flower hybrid tea; viewed from above — round; viewed from side — (a) upper part of fully opened flower, flat; (b) lower part of fully opened flower, flattened convex.

(1) *Size.*—Average size when fully expanded — about 9 to 10 cm.

(2) *Bourne.*—Singly, one to a stem, stem length about 50 cm.

(3) *Form.*—Ovoid bud opens to urn shaped, becoming flat upon opening; some outer petals reflex and inner petals roll under slightly.

(4) *Petalage.*—Many petaled under normal conditions — fully semi-double, about 35 petals.

(5) *Color.*—After sepals separate, near 36A; when sepals part and petals begin to unfurl, color is near 36A; petals' top surface near 36C, 37C and 38C with apricot toward center and pink otherwise; reverse sides tend to apricot pink. Coloring at point of petal attachment is near 2C. Overall tonality from a distance is attractive apricot to apricot pink, near 50D.

(6) *Pedicel.*—Very few hairs or prickles.

(7) *Fragrance.*—Weak.

C. Petals:

(1) *Texture.*—Medium.

(2) *Appearance.*—Inside velvety and outside satiny.

(3) *Form and size.*—Small, transverse elliptic.

(4) *Arrangement.*—Regularly arranged, inbricated.

(5) *Petaloids in center.*—Few to none.

(6) *Lasting quality.*—Long lasting quality on plant and after cutting.

Reproductive Organs

A. Stamens, filaments and anthers:

*Arrangement and color.*—Regularly arranged around styles; color of filaments — yellow.

B. Pollen:

*Color.*—Yellow orange.

C. Styles: Medium, yellow, only slightly hairy.

D. Stigmas: Positioned at same level as anthers.

E. Hips: Medium, urn shaped.

Plant

A. Form: Upright to bushy.

B. Growth: Vigorous, about 1.5 m high by about 45 cm wide.

C. Foliage: Compound 3, and 5 leaflets.

(1) *Size.*—Medium.

(2) *Quantity.*—Abundant.

(3) *Color.*—Foliage at time of first flowering — medium green, mature foliage — near 139A.

(4) *Shape.*—Oval, pointed.

(5) *Texture.*—Upper side is weakly glossy; underside is matte.

(6) *Edge.*—Serrate.

(7) *Serration.*—Ordinary, acuminate apices.

(8) *Leaf stem.*—Color — medium green.

(9) *Stipules.*—Short, simple, medium to light green, distinct auricle.

(10) *Leaflets.*—Cross section — concave, medium undulation at margin; terminal leaflet (length of blade) — medium length, wide width; petiole — medium, base wedge shaped.

D. Wood:

(1) *New wood.*—Color — dark green, near 139C to B, young shoots have weak anthocyanin coloration — reddish brown.

(2) *Old wood.*—Color — medium green, near 137A.

E. Prickles (thorns):

(1) *Prickles.*—Present; quantity (main stalk) — ordinary. On laterals from stalk — ordinary. Form — straight. Shape of upper side — flat. Shape of lower side — concave to flat. Length — $\leqq 5$ mm, very few; $>5$ mm, medium. Color — tan to pale pink, depending on position on stem. Position — irregular.

I claim:

1. A new and distinct variety of rose plant of the hybrid tea rose class, substantially as shown and described.

* * * * *

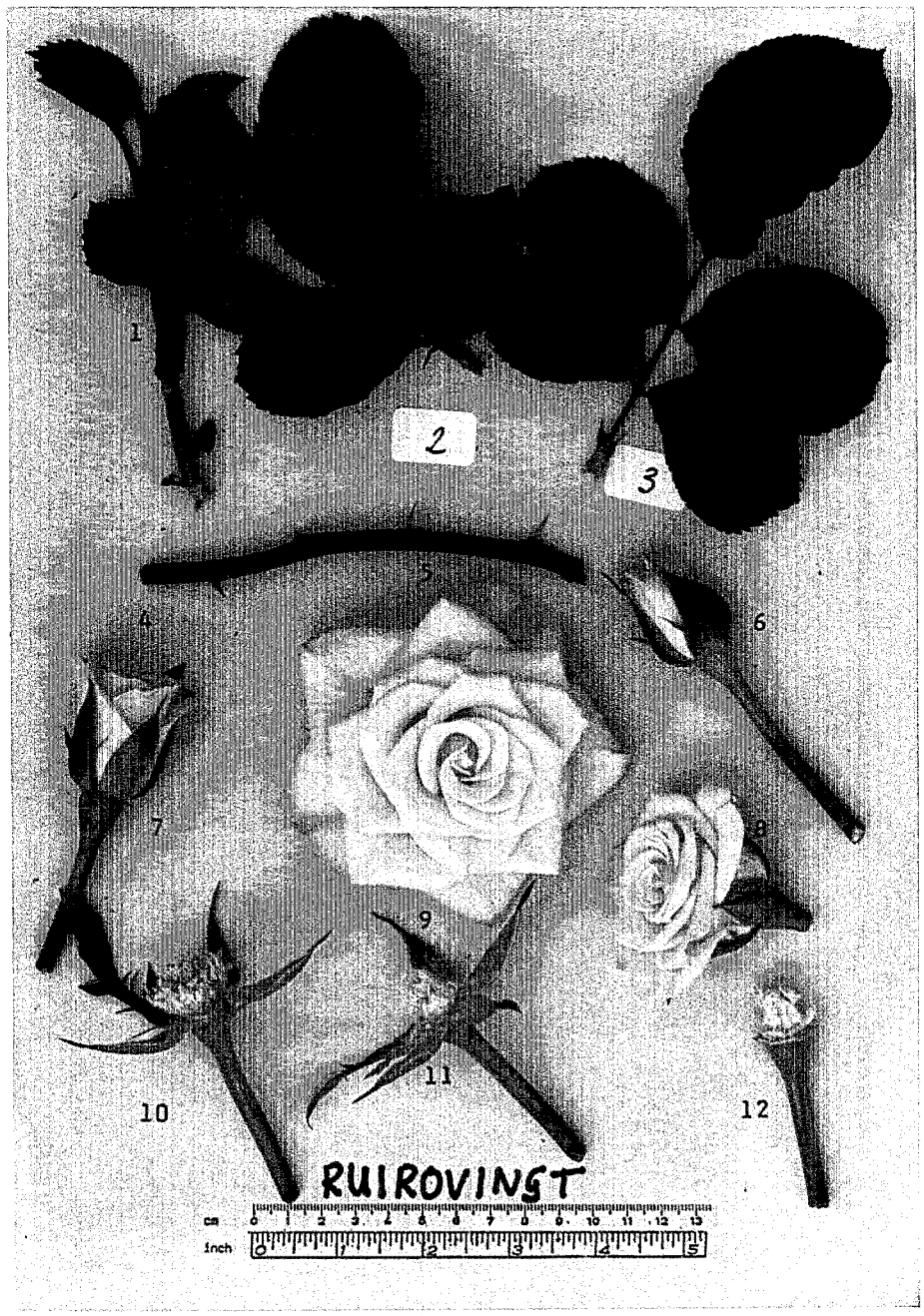
1
2
3
4
5
6
7
8
9
10
11
12
RUIROVINGT
cm
inch

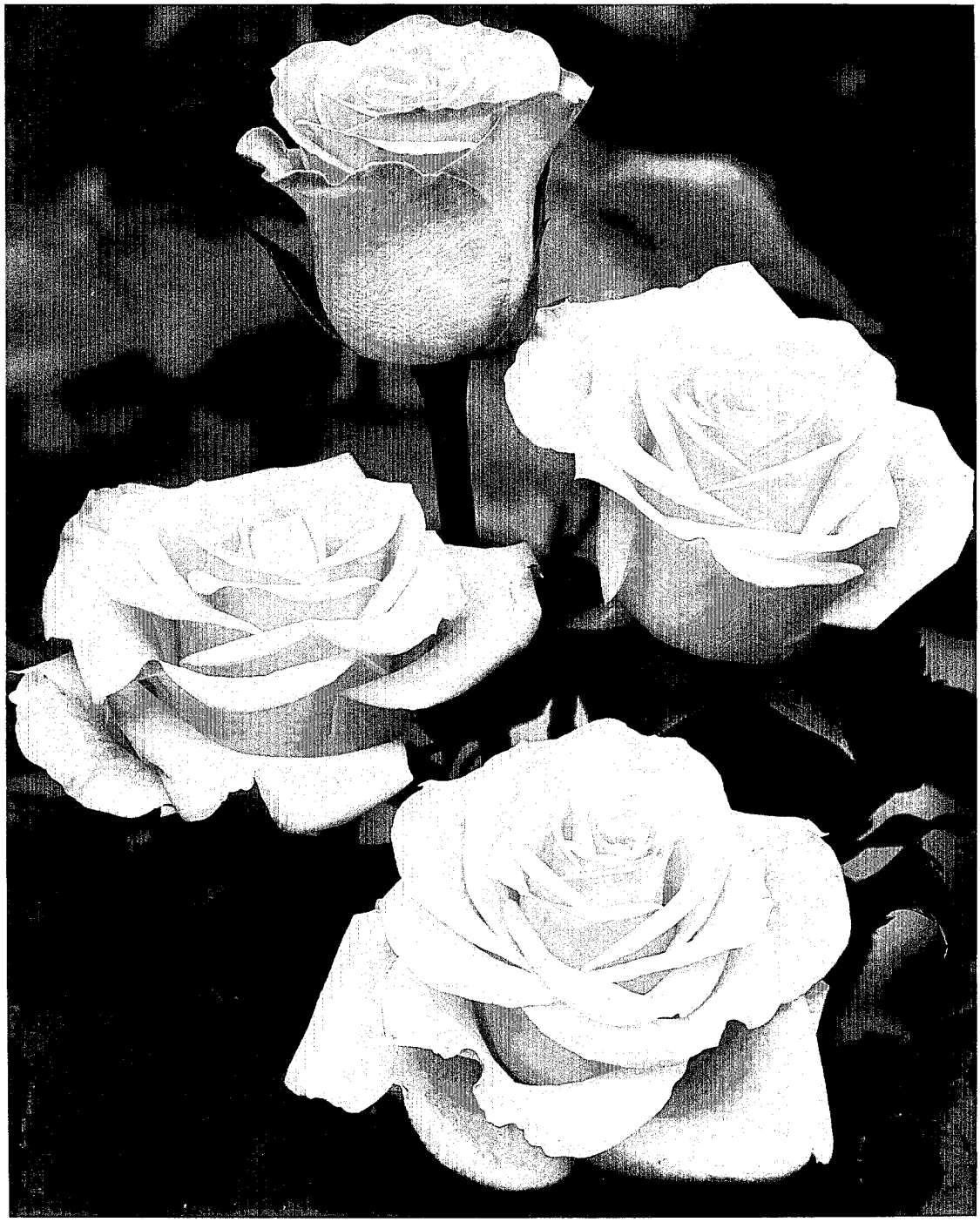

UNITED STATES PATENT AND TRADEMARK OFFICE

CERTIFICATE OF CORRECTION

PATENT NO. : Plant 8,528

DATED : January 4, 1994

INVENTOR(S) : Gijsbert de Ruiter

It is certified that error appears in the above-indentified patent and that said Letters Patent is hereby corrected as shown below:

Column 1, line 23, change "distinguuishing" to -- distinguishing --.

Column 2, line 41, change "Bourne" to -- Borne --.

Signed and Sealed this

First Day of November, 1994

*Attest:*

*Attesting Officer*

BRUCE LEHMAN

*Commissioner of Patents and Trademarks*